United States Patent [19]

Yamada

[11] 4,378,019
[45] Mar. 29, 1983

[54] HAIR IMPLANTING APPLIANCE

[76] Inventor: Shiro Yamada, 31-8, Koboyama, Kobo-cho, Chiryu-shi, Aichi-ken, Japan

[21] Appl. No.: 165,241

[22] Filed: Jul. 2, 1980

[30] Foreign Application Priority Data

Jul. 3, 1979 [JP] Japan .................................. 54-83509

[51] Int. Cl.³ ............................................ A61B 17/00
[52] U.S. Cl. ................................................... 128/330
[58] Field of Search ................... 128/330, 339, 329 R; 46/172; 132/53, 56; 112/48, 169; 223/102, 104

[56] References Cited

U.S. PATENT DOCUMENTS 3,513,860  5/1970  Kost ................................. 132/56 X
4,216,777  8/1980  Pridemore ........................... 128/330
4,221,212  9/1980  Miller ............................. 128/330 X

FOREIGN PATENT DOCUMENTS 1953026  2/1972  Fed. Rep. of Germany ...... 128/330
2843072  4/1979  Fed. Rep. of Germany ...... 128/330
 765220  1/1957  United Kingdom ............ 128/329 R Primary Examiner—Michael H. Thaler
Attorney, Agent, or Firm—Browdy & Neimark

[57] ABSTRACT

A hair implanting appliance for directly implanting an artificial hair in a human skin comprises a needle formed at its leading end with a notch which is sized and shaped to retain the root portion of the hair. The needle is snugly and slidably received in the through hole of a sheath such that its leading end can protrude from the leading end of the sheath into the human skin to a depth necessary for the hair implantation. The sheath has at least a portion of its leading open end merge into the open edge of the notch at the leading end of the needle when this needle is retracted into the sheath and this structure forms the guide surface of the root portion retained in the notch.

3 Claims, 18 Drawing Figures

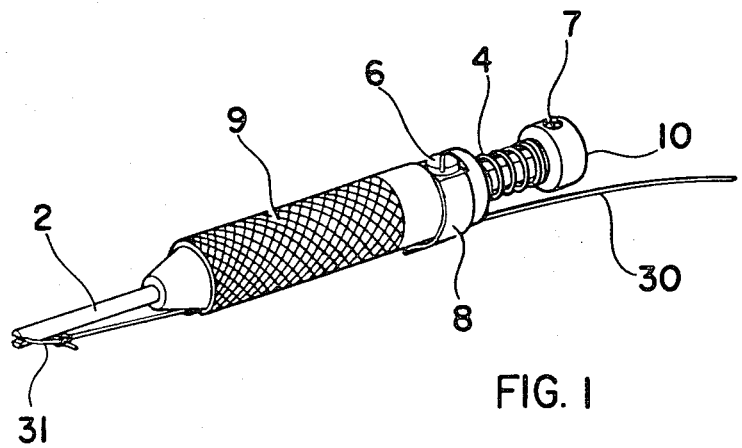
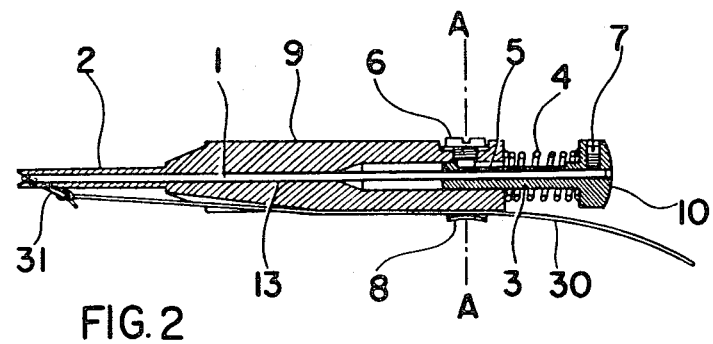
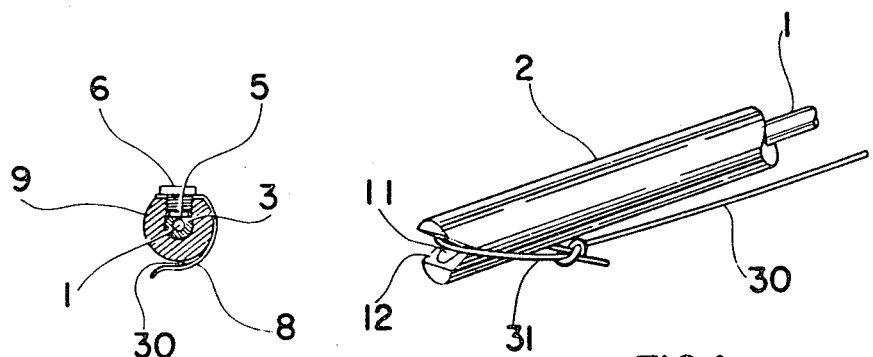
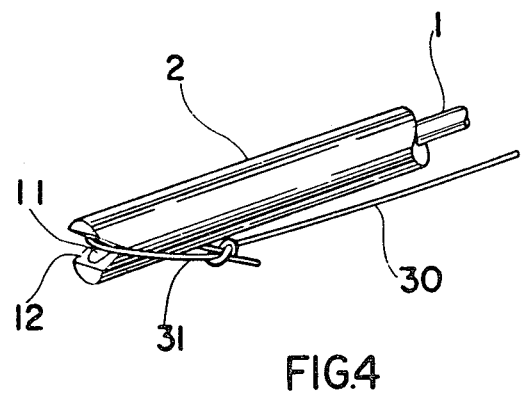
FIG. 1
FIG. 2
FIG. 3
FIG. 4

HAIR IMPLANTING APPLIANCE

DESCRIPTION

Field of the Invention

The present invention relates to improvements in a hair implanting appliance for directly implanting artificial hairs into human skin.

Background of the Invention

The technique for directly implanting artificial hairs in human skin has been remarkably developed in recent years, and various types of artificial hairs and their implanting appliances have accordingly been improved in a number of forms. As to the shapes of the root portions of the hairs, for instance, various proposals have been made including providing an ampoule shape (U.S. Pat. No. 4,024,315), an arrowhead shape (Japanese Patent Publication No. 54-11744), a looped shape and a knot which is formed at the root portion.

As to hair implanting appliances, on the other hand, various developments have been made including a hollow needle (U.S. Pat. No. 4,004,592), an air gun type hair implanter (Japanese Patent Publication No. 54-11744), a hair implanting needle formed with a recess at its tip (U.S. Pat. No. 4,004,592), a pincette-shaped hair implanting needle (U.S. Pat. No. 4,004,592) and a bifurcated needle (U.S. Pat. No. 4,004,592).

The most slender hair implanting needle according to the prior art has an outside limit diameter of 0.3 mm for the case of a hollow structure and a limit diameter of 0.35 to 0.5 mm for the case of a bifurcated or similar structure. This is because it becomes difficult to insert any artificial hair into the hollow needle which has a smaller outside diameter than the above-specified value. In the case of a bifurcated needle, having a smaller diameter than the above-specified value, it may bend when the needle is pierced into the skin, so that it cannot carry out its function. If, moreover, the thickness of the needle is excessively reduced, the retaining operation of the artificial hair at the tip of the bifurcated needle becomes so dificient as to cause the hair implanting operations to be deteriorated.

In order to enhance the fixation percentage of the artificial hairs implanted, emphasis has been placed upon the shape of the hair root portion for increasing its resistance to extraction and upon research for the developments of needles which are best suited for implanting the artificial hairs.

Summary of the Invention

Although the shape of the hair root portion plays an important role in enhancing the fixation percentage of the hairs, it has now been discovered that the fixation percentage is more dependent upon the extent of breakage of the epidermis and hypodermal tissue of the human skin. More specifically, if the epidermis and the hypodermal tissue are heavily broken when they receive the artificial hair, it takes much time for the wound to be restored so that the implanted root portion may be removed by external force before it is sufficiently fixed, with the resultant deterioration in the fixation percentage immediately after the hair implantation. Moreover, if this instable or unfixed term is long, inflammation or suppuration is liable to take place causing further reduction in the hair fixation percentage.

With this in mind, it is therefore necessary to minimize the thickness of the hair implanting needle and to devise both the shape of the hair root portion which can minimize the wound when the hair is implanted and the shape of the hair implanting needle which can be used in combination with that root portion. Yet this must be done without violation of the reasons prior implanting needles have not been made smaller, as noted above.

It is, accordingly, an object of the invention to overcome deficiencies in the prior art, such as indicated above; a further object is to provide for improved implantation of artificial hair.

It is another object of the present invention to provide a hair implanting appliance which can maintain the strength necessary for the hair implantation and can facilitate the retaining operation of an artificial hair at the tip of a needle even if the thickness of the needle is reduced.

According to a major aspect of the present invention, there is provided a hair implanting appliance comprising: means to penetrate the scalp comprising a needle having its leading end formed with a notch which is sized and shaped to retain the root portion of an artificial hair to be implanted; and means to guide the needle without penetrating the scalp comprising a sheath formed with a through hole which has substantially the same inside diameter as the outside diameter of said needle, the needle being slidably received in the sheath such that the leading end of the needle can be extended from the leading end of the sheath which abuts the scalp into a human skin to a depth necessary for the hair implantation and such that the sheath has at least a portion of its leading open end, which is to merge into the open edge of the notch at the leading end of the needle when the needle is retracted into the sheath, forming the guide surface of the root portion to be retained. Such guide surface portion of the leading end of the sheath cooperates with the notch in the leading end of the needle to better control the positioning of the hair root in the appliance.

The most satisfactory artificial hair that can be implanted by the appliance according to the present invention is prepared such that its leading end is curled to form a looped root portion. Artificial hairs having other shapes can also be used if their necks leading to the root portions can be retained by the leading end notch of the needle.

On the other hand, the needle to be used in the hair implanting appliance according to the present invention may be formed with a V-shaped notch either at the tip or in the side wall of the leading end thereof.

A satisfactory sheath for the afore-mentioned hair implanting needle provided with the V-shaped notch at the tip thereof may be formed at its leading open end with a V-shaped notch. If this sheath is used, the afore-mentioned open end of the sheath having the V-shaped notch is positioned to line up with the V-shaped notch at the tip of the needle, when said needle is retracted into the sheath, so that it acts as a guide surface when the looped root portion of the artificial hair is to be retained in the needle tip, thereby facilitating the retaining operation of the root portion in the needle tip.

Moreover, a sheath which has its leading open end obliquely cut can be used in a similar manner. In this case, one side of the V-shaped notch of the needle merges into the open end of the sheath thereby to form a guide surface in which the root portion is retained. The other side of the notch of the needle protrudes beyond the sheath to easily receive the root portion and retain it in the notch.

The sheathes thus far described can also be used in the case of the needle which is formed along its side wall with a V-shaped notch. In addition, there can be used a sheath which has its leading end so cut only at the semicircumference that the open end of the cut merges into the lower edge of the open portion of the V-shaped notch. In case a sheath of this type is used, the remaining semicircumference of the sheath partly protects the tip of the hair implanting needle and partly further facilitates the retaining operation of the looped root portion in the needle tip.

The most desirable shape of the V-shaped notch of the hair implanting needle is made such that its inlet is wide enough to receive the root portion of the hair to be retained without any difficulty and that it becomes increasingly narrowed. However, the shape of the notch may be freely modified from the machining requirements such that it has the same width at the inlet and at the bottom and such that the bottom is angled or rounded if the modification is within such a range as to raise no obstacle to the reception of the root portion of the hair.

In the hair implanting appliance according to the present invention, the needle is slidably received in the sheath. A dolly member formed with a bulged portion having an enlarged diameter is fixed to the base portion of the needle. A spring is mounted between the sheath and the dolly member thereby to urge the needle into the sheath at all times.

At the most retracted position, in which the needle is retracted into the sheath, as has been described above, the leading open end of the sheath forms the guide surface for guiding the artificial hair into the notch, which is formed at the tip of the needle for retaining the hair. It is therefore necessary to make such a construction that the sheath and the needle are prevented from shifting in the circumferential direction relative to each other. While this objective may be accomplished in a variety of ways, according the simplest method either the needle or the dolly member fixed to the former is cut at its side wall in the longitudinal direction to form either a flat portion or a key way. This flat portion or key way is made coactive with the member, which is disposed to protrude into the through hole of the sheath, so that the needle may slide in the axial direction but not in the circumferential direction.

According to the hair implanting appliance of the present invention having the construction thus far described, since the sheath effectively increases the strength of the hair implanting needle, the diameter of the needle can be reduced to less than two thirds the conventional one, i.e. to only 0.2 to 0.25 mm.

BRIEF DESCRIPTION OF THE DRAWINGS

FIG. 1 is a perspective view showing a hair implanting appliance according to the present invention;

FIG. 2 is a longitudinal section of FIG. 1;

FIG. 3 is a transverse section along line A—A of FIG. 2;

FIG. 4 is an enlarged perspective view showing the tip portion of the needle;

DESCRIPTION OF THE PREFERRED EMBODIMENTS

Figure 5:
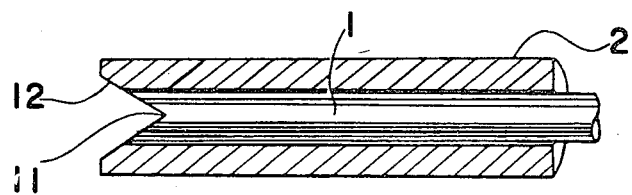
FIGS. 5 to 10 are partially sectional views showing various modifications of the needle tip and the open end of the sheath.

The embodiments of the present invention will now be described with reference to the accompanying drawings.

Referring first to FIGS. 1 to 4, a hair implanting needle 1 is formed at its leading end with a V-shaped notch 11 and is fixed at its base to a dolly member 3 by means of a screw 7. The needle 1 is slidably received in the through hole 13 which is formed in both a sheath 2 and a handle member or grip 9 integral therewith. By the engagement between a key way 5, which is formed in the dolly member 3 fixed to the needle 1, and a screw 6 which is fastened into the grip 9 from the outside and extends into the through-hole 13, the needle 1 is prevented from rotating relative to the sheath 2, and the stroke of the needle 1 between the most protruding position and the most retracted position is preset.

Between the head 10 of the dolly member 3 and the grip 9, there is mounted a coil spring 4 for urging or biasing the needle 1 into the sheath 2 to its most retracted position. As a result, under the most retracted position shown in FIG. 4, a V-shaped notch 12 formed at the leading open end of the sheath 2 is positioned to merge with the V-shaped notch 11 which is formed at the leading end of the needle 1 so that it acts as a guide surface for guiding the root portion 31 of an artificial hair 30 into the bottom of the V-shaped notch 11 of the needle 1.

The device is also provided with a retainer element 8 in the form of a leaf spring. The artificial hair 30 thus retained by its root portion 31 in the V-shaped notches 11 and 12 has its body portion gently held on the handle 9 by means of the rounded leaf spring 8.

FIG. 5 is a longitudinal section showing the same embodiment as that of FIG. 4 in an enlarged scale, whereas FIGS. 6 to 10 show other embodiments of the hair implanting needle and its sheath. In FIG. 5, it is seen that the notch 12 of the sheath 2 separates the tip of the sheath 2 into two facing semi-circular lips.

Figure 6:
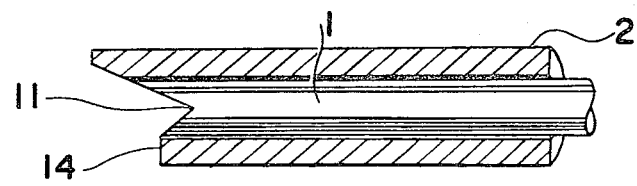

In the embodiment shown in FIG. 6, more specifically, the needle 1 is substantially the same as that of FIG. 5 in that it is formed at its tip with a V-shaped notch 11. However, one of the lips of the tip of the sheath 2 is removed i.e. a portion corresponding to one side of the V-shaped notch, to thereby form semi-circular flat edge 14. This structure enables the looped root portion 31 to be hooked obliquely over the flat portion 14 with more ease compared to the FIG. 5 structure.

Figure 7:
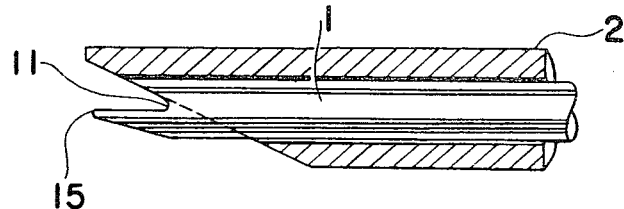

In the embodiment shown in FIG. 7, on the other hand, the tip end of the sheath 2 is obliquely cut. A V-shaped notch 11 of the needle 1 has its one side protruding to form a protrusion 15, on which the looped root portion 31 is hooked and retained. According to this embodiment, the looped root portion 31 is placed over the tip of the needle 1 with the needle 1 slightly protruding beyond the sheath 2. When the needle 1 is then retracted into the sheath 2 to the position shown in FIG. 7, the root portion 31 is guided by the open end of the sheath 2 until it naturally falls into the V-shaped notch 11 where it can be retained.

Figure 8:
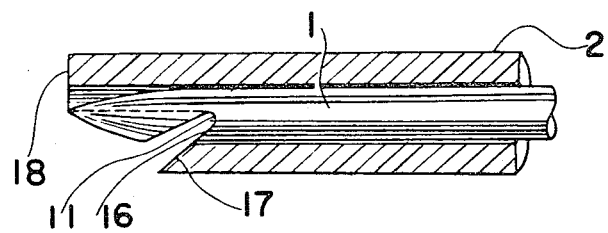

FIG. 8 shows another embodiment, in which a V-shaped notch 11 is formed in the side wall of the pointed leading end of the needle 1. The corresponding sheath 2 is cut at its semi-circumference adjacent the notch 11 that its cut open edge 17 merges into the lower edge 16 of the open portion of the V-shaped notch 11. The open edge 17 acts as the guide surface for retaining the root portion 31 of the hair in the notch 11. In this instance, the remaining semicircumference 18 of the sheath 2 functions to protect the tip of the needle 1 and maintain it out of danger.

Figure 9:
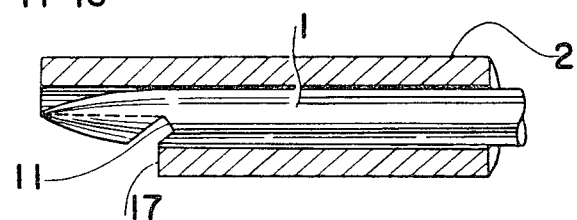

FIG. 9 shows a modification of the embodiment of FIG. 8, in which a lip of the sheath 2 is transversely cut to form a semi-circular edge 17. According to this modification, the V-shaped notch 11 is shaped to have the same width at its inlet and at its bottom.

Figure 10:
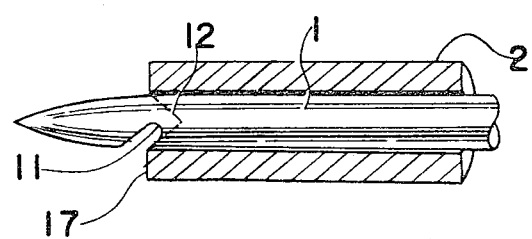

FIG. 10 shows another modification of the embodiment of FIG. 8, in which both semi-circular lips of the sheath 2 are wholly cut off to form a pair of semi-circular flat edges 17, like the semi-circular flat edge 14 in FIG. 6, separated by the V-shaped notch 12. The sheath 2 in this modification is provided in its side wall with the V-shaped notch 12 which merges into the V-shaped notch 11 in the side wall of the needle 1.

Figures 11, 12, 13, 14, 15:
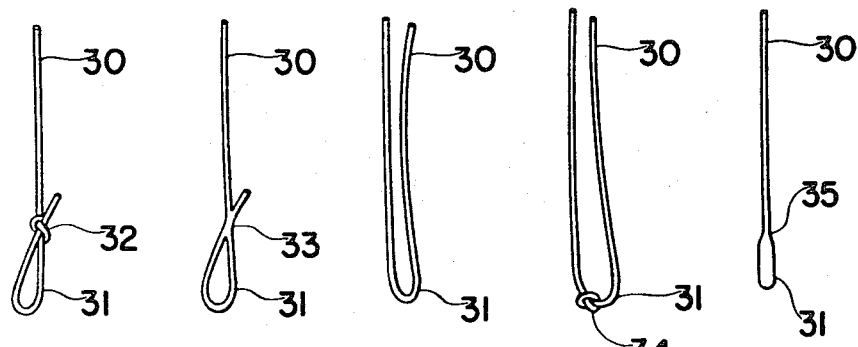
FIGS. 11 to 15 are illustrative views showing various artificial hairs to be used with the appliance of the present invention.

Turning now to FIGS. 11 and 12, the preferred artificial hair for the present invention is prepared such that the leading end of the artificial hair 30 is curled to form the looped root portion 31. The example shown in FIG. 11 is formed by knotting the looped root portion 31 as at 32, whereas the example shown in FIG. 12 is formed by melting or adhering the root portion 31 as at 33.

FIG. 13 shows another example of the artificial hair 30 in case a long monofilament has its middle portion hooked by the tip of the needle and thrust into the skin so that the bent portion forms the root portion 31.

FIG. 14 is an example which is improved from the example of FIG. 13 such that the bent portion is knotted at 34 to form the root portion 31.

In a further example shown in FIG. 15, the artificial hair 30 is formed at its leading end with the root portion 31 which is bulged into an anpoule shape. If the hair 30 is retained at the neck 35 of its root portion 31 in the V-shaped notch 11 of the hair implanting needle 1 of the present invention, it can be implanted in a similar manner to those of the foregoing examples.

Use of the hair implanting appliance according to the present invention is as follows.

Figures 16, 17, 18:
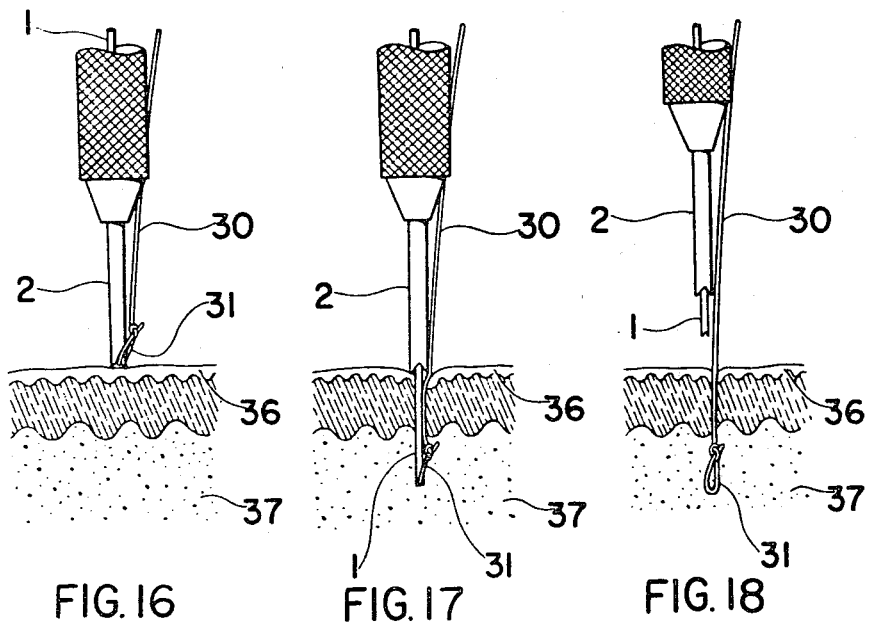
FIGS. 16 to 18 are explanatory views illustrating the using method of the appliance of the present invention.

As shown in FIG. 16, the leading end of the sheath 2 is applied to the epidermis 36 of a human skin with the looped root portion 31 of the artificial hair 30 being hooked in the V-shaped notch 11 of the needle tip. When the dolly member 3 fixing the needle 1 is pushed down by the finger of an operator, the needle 1 is thrust into the hypodermal tissue 37 while carrying the root portion 31, as shown in FIG. 17. This thrust of the root portion 31 is continued until it reaches the hypodermal tissue 37 which is located 4 to 7 mm beneath the epidermis 36. This distance or stroke is automatically determined by presetting the length of the key way Although the needle 1 is as thin as 0.2 to 0.25 mm, as has been described before, it is reinforced by its sheath 2 so that it can be prevented from warping.

After the root portion 31 has reached the present position, the needle 1 is gently extracted, as shown in FIG. 18, thus completing the hair implanting operation.

If the hair implanting operation is performed with the use of the hair implanting appliance according to the present invention, the thickness of the needle is so small that the breakage in the epidermis or the hypodermal tissue due to the hair implantation is minimized with the satisfactory result that the fixation percentage of the implanted hairs is high.

It will be obvious to those skilled in the art that various changes may be made without departing from the scope of the invention and the invention is not to be considered limited to what is shown in the drawings and described in the specification.

I claim:

1. A hair implanting appliance comprising:

means to penetrate the scalp comprising a needle having its leading end formed with a generally V-shaped notch formed by a pair of surfaces at least one of which is inclined and at least one of which extends from the tip of said needle, said V-shaped notch being sized and shaped to retain the root of an artificial hair to be implanted;

means to guide said needle without penetrating the scalp comprising a sheath formed with a through hole which has substantially the same inside diameter as the outside diameter of said needle, said sheath having a scalp abutting leading end and at least one inclined guide surface extending rearwardly from said scalp abutting end, said needle being slidably received in said sheath (i) such that the leading end of said needle can protrude from said scalp abutting leading end of said sheath and project into a human skin to a depth necessary for the hair implantation and (ii) such that said inclined guide surface of said sheath merges with and forms a continuation of said inclined surface of the V-shaped notch at the leading end of said needle when said needle is retracted into said sheath, whereby said inclined guide surface of the leading end of said sheath and said inclined surface of said V-shaped notch at the leading end of said needle form an enlarged guide portion for the hair root to be retained by said appliance and cooperate to control the positioning of the hair root in said appliance; and means to reciprocate said needle axially to cause the leading end of said needle to protrude from the leading end of said sheath;

wherein said needle has an exterior diameter of 0.2-0.25 mm; and wherein the leading open end of said sheath is formed into a V-shaped notch.

2. A hair implanting appliance comprising:

means to penetrate the scalp comprising a needle having its leading end formed with a generally V-shaped notch formed by a pair of surfaces at least one of which is inclined and at least one of which extends from the tip of said needle, said V-shaped notch being sized and shaped to retain the root of an artificial hair to be implanted;

means to guide said needle without penetrating the scalp comprising a sheath formed with a through hole which has substantially the same inside diameter as the outside diameter of said needle, said sheath having a scalp abutting leading end and at least one inclined guide surface extending rearwardly from said scalp abutting end, said needle being slidably received in said sheath (i) such that the leading end of said needle can protrude from said scalp abutting leading end of said sheath and project into a human skin to a depth necessary for the hair implantation and such that said inclined guide surface of said sheath merges with and forms a continuation of said inclined surface of the V-shaped notch at the leading end of said needle when said needle is retracted into said sheath, whereby said inclined guide surface of the leading end of said sheath and said inclined surface of said V-shaped notch at the leading end of said needle form an enlarged guide portion for the hair root to be retained by said appliance and cooperate to control the positioning of the hair root in said appliance; and means to reciprocate said needle axially to cause the leading end of said needle to protrude from the leading end of said sheath;

wherein said needle has an exterior diameter of 0.2-0.25 mm; and wherein the leading open end of said sheath has only its one semicircumference cut both at an inwardly inclined plane and at a plane containing the center axis of said sheath.

3. A hair implanting appliance comprising:

means to penetrate the scalp comprising a needle having its leading end formed with a generally V-shaped notch formed by a pair of surfaces at least one of which is inclined and at least one of which extends from the tip of said needle, said V-shaped notch being sized and shaped to retain the root of an artificial hair to be implanted;

means to guide said needle without penetrating the scalp comprising a sheath formed with a through hole which has substantially the same inside diameter as the outside diameter of said needle, said sheath having a scalp abutting leadin end and at least one inclined guide surface extending rearwardly from said scalp abutting end, said needle being slidably received in said sheath (i) such that the leading end of said needle can protrude from said scalp abutting leading end of said sheath and project into a human skin to a depth necessary for the hair implantation and (ii) such that said inclined guide surface of said sheath merges with and forms a continuation of said inclined surface of the V-shaped notch at the leading end of said needle when said needle is retracted into said sheath, whereby said inclined guide surface of the leading end of said sheath and said inclined surface of said V-shaped notch at the leading end of said needle form an enlarged guide portion for the hair root to be retained by said appliance and cooperate to control the positioning of the hair root in said appliance; and means to reciprocate said needle axially to cause the leading end of said needle to protrude from the leading end of said sheath; and wherein the angle of inclination of said inclined guide surface of said sheath is the same as the angle of inclination of said inclined surface of said V-shaped notch.

* * * * *